United States Patent
Chen (10) Patent No.: US 12,419,375 B2
(45) Date of Patent: Sep. 23, 2025

(54) LUMBAR SUPPORT BELT

(71) Applicant: CONWELL MEDICAL CO., LTD., Taichung (TW)

(72) Inventor: Chien-Cheng Chen, Taichung (TW)

(73) Assignee: CONWELL MEDICAL CO., LTD., Taichung (TW)

( * ) Notice: Subject to any disclaimer, the term of this patent is extended or adjusted under 35 U.S.C. 154(b) by 193 days.

(21) Appl. No.: 18/527,261

(22) Filed: Dec. 2, 2023

(65) Prior Publication Data

US 2024/0389694 A1 Nov. 28, 2024

(30) Foreign Application Priority Data

May 25, 2023 (TW) .................................. 112119516

(51) Int. Cl.
*A41F 9/02* (2006.01)
*A61F 5/02* (2006.01)

(52) U.S. Cl.
CPC .............. *A41F 9/025* (2013.01); *A61F 5/028* (2013.01)

(58) Field of Classification Search
CPC .... A41F 9/025; A41F 9/02; A41F 9/00; A61F 5/028; A61F 5/02; A61F 5/01; A61F 5/00
See application file for complete search history.

(56) References Cited

U.S. PATENT DOCUMENTS

2018/0085243 A1* 3/2018 Burke ...................... A61F 5/028
2021/0177637 A1* 6/2021 Derrico ................... A61F 5/026

FOREIGN PATENT DOCUMENTS

CN 112869928 A * 6/2021 ............. A61F 5/028

* cited by examiner

*Primary Examiner* — Tarla R Patel (57) ABSTRACT

A lumbar support belt includes a backing plate, two belt bodies, and a tightening part. The backing plate includes at least one sliding channel. The two belt bodies are respectively connected to a left side and a right side of the backing plate. Each belt body has multiple routing portions and at least one sliding wheel disposed in the at least one sliding channel. The tightening part wraps around the routing portions of the two belt bodies to connect the two belt bodies and has two pulling segments. The at least one sliding wheel of each of the two belt bodies respectively slides along the at least one sliding channel of the backing plate toward the other one of the two belt bodies while pulling the two pulling segments of the tightening part away from the backing plate.

12 Claims, 12 Drawing Sheets

LUMBAR SUPPORT BELT

BACKGROUND

1. Field of the Invention

The present invention relates to a protective gear, and more particularly to a lumbar support belt that is tightness adjustable.

2. Description of Related Art

A lumbar support belt is a protective gear wrapped on the lower back of a human body to provide support to the lumbar, to limit the angle of body movement, and to protect the waist, thereby reducing lower back pain of a user.

Figure 12:
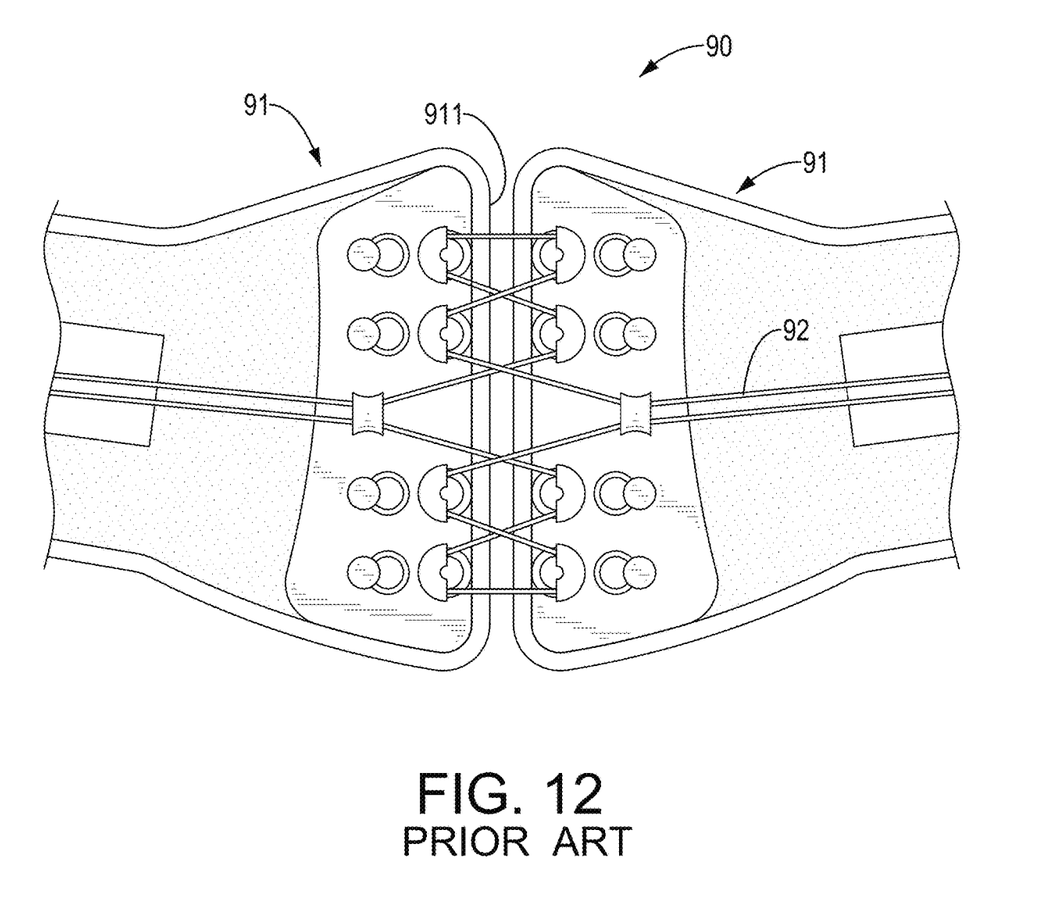
FIG. 12 is an enlarged elevation view of a conventional lumbar support belt.

With reference to FIG. 12, a conventional lumbar support belt 90 substantially comprises two belt bodies 91 and a tightening cable 92 connected with the two belt bodies 91. Each belt body 91 includes a connecting end 911 and a fastening end. The two belt bodies 91 respectively have touch fastening surfaces attached to each other for fastening. The tightening cable 92 is cross-laced at the connecting ends 911 of the two belt bodies 91 for connecting the two belt bodies 91. The tightening cable 92 has two tightening segments respectively extending toward the two belt bodies 91. A fastener is connected to an end of each tightening segment.

After the conventional lumbar support belt 90 is wrapped around a user's waist, the touch fastening surfaces of the two belt bodies 91 are adhered to and attached to each other to wrap the conventional lumbar support belt 90 around the user's waist. To adjust the tightness of the conventional lumbar support belt 90, the two tightening segments of the tightening cable 92 are pulled toward opposite directions to move the connecting ends 911 of the two belt bodies 91 close to each other for tightening. Then, the fasteners at the ends of the two tightening segments are adhered to and attached to the touch fastening surfaces of the two belt bodies 91, accomplishing the adjustment.

However, while pulling the tightening cable 92 for adjusting relative position between the two belt bodies 91, the tightening cable 92 gets stuck easily, increasing resistance. The user cannot easily and smoothly adjust the tightness. Moreover, when the connecting ends 911 of the two belt bodies 91 are moved close to each other, the two belt bodies 91 are prone to misalignment due to uneven forces.

To overcome the shortcomings of the conventional socket holding frame, the present invention provides a lumbar support belt to mitigate or obviate the aforementioned problems.

SUMMARY

The present invention relates to a lumbar support belt that has two belt bodies which can be smoothly moved toward each other by the user.

The lumbar support belt comprises a backing plate, two belt bodies, and a tightening part. The backing plate includes at least one sliding channel extending horizontally. The two belt bodies are respectively connected to a left side and a right side of the backing plate. Each of the two belt bodies includes multiple routing portions arranged top-down at spaced intervals and at least one sliding wheel disposed in the at least one sliding channel. The tightening part wraps around the routing portions of the two belt bodies to connect the two belt bodies and has two pulling segments respectively extending toward the two belt bodies. The at least one sliding wheel of one of the belt bodies slides along the at least one sliding channel of the backing plate toward the other one of the two belt bodies while pulling the two pulling segments of the tightening part away from the backing plate.

Other objects, advantages, and novel features of the invention will become more apparent from the following detailed description when taken in conjunction with the accompanying drawings.

DETAILED DESCRIPTION

With reference to FIGS. 1 to 5, a first embodiment of a lumbar support belt in accordance with the present invention comprises a backing plate 10, two belt bodies 20, and a tightening part 30.

The backing plate 10 includes at least one sliding channel 12L/12R extending horizontally.

The two belt bodies 20 are respectively connected to a left side and a right side of the backing plate 10. Each belt body 20 includes multiple routing portions 23 arranged top-down at spaced intervals and at least one sliding wheel 25 disposed in the at least one sliding channel 12L/12R. Specifically, the at least one sliding channel 12L/12R may include multiple sliding channels 12L/12R spaced apart from one another, which may be longitudinally arranged top-down at spaced intervals and/or laterally arranged left and right at spaced intervals. When the backing plate 10 includes multiple sliding channels 12L/12R arranged top-down at spaced intervals, each belt body 20 may include multiple sliding wheels 25 respectively mounted in the multiple sliding channels 12L/12R. In the first embodiment, the backing plate 10 includes multiple sliding channels 12L adjacent to the left side of the backing plate 10 and arranged top-down at spaced intervals and multiple sliding channels 12R adjacent to the right side of the backing plate 10 and arranged top-down at spaced intervals. The multiple sliding channels 12L adjacent to the left side of the backing plate 10 are spaced apart from and respectively aligned with the multiple sliding channels 12R adjacent to the right side of the backing plate 10. One of the two belt bodies 20 includes multiple sliding wheels 25 respectively disposed in the multiple sliding channels 12L adjacent to the left side of the backing plate 10. The other one of the two belt bodies 20 includes multiple sliding wheels 25 respectively disposed in the multiple sliding channels 12R adjacent to the right side of the backing plate 10.

Figure 6:
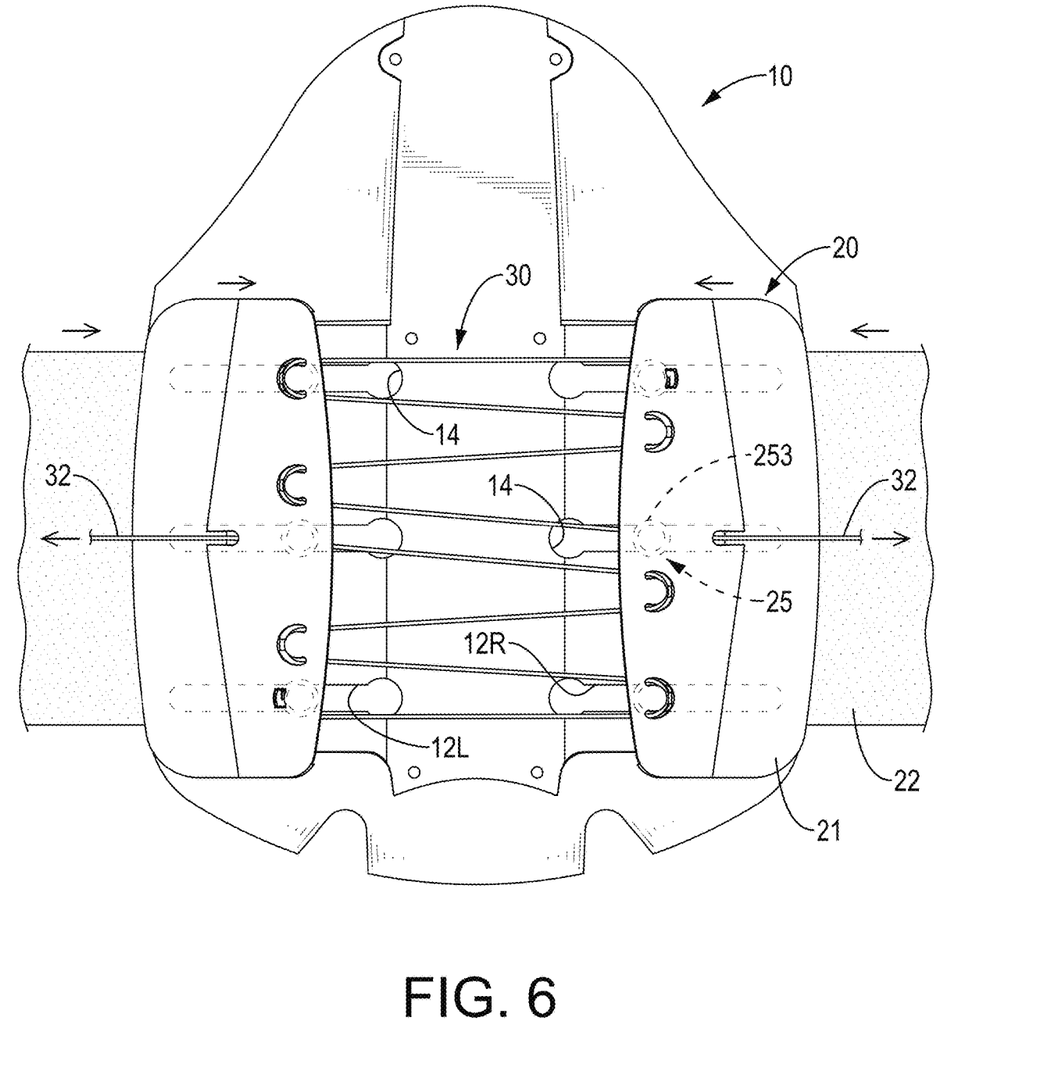
FIG. 6 is an enlarged operational elevation view of the lumbar support belt in FIG. 1.
Figure 7:
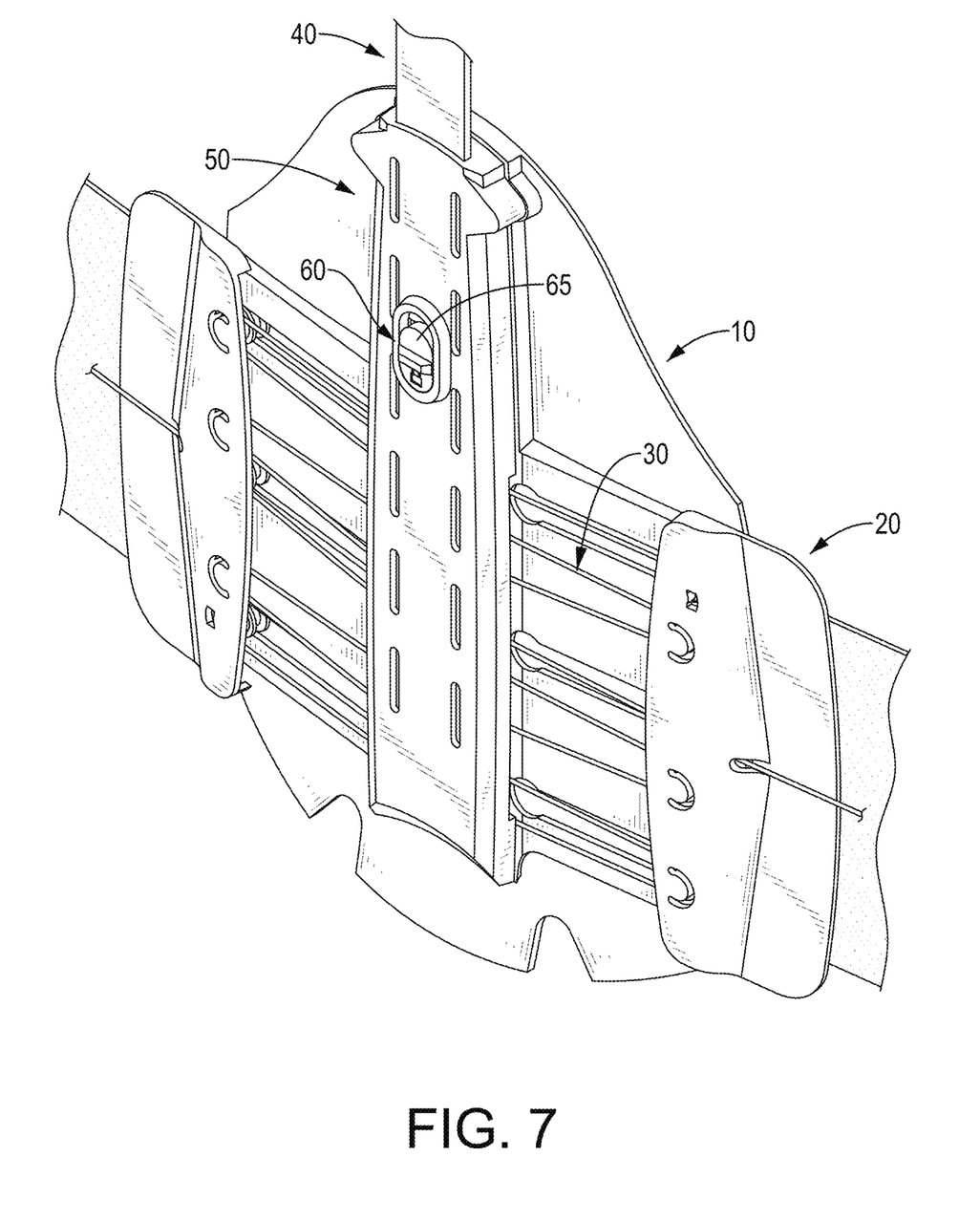
FIG. 7 is an enlarged perspective view of a second embodiment of a lumbar support belt in accordance with the present invention.
Figure 8:
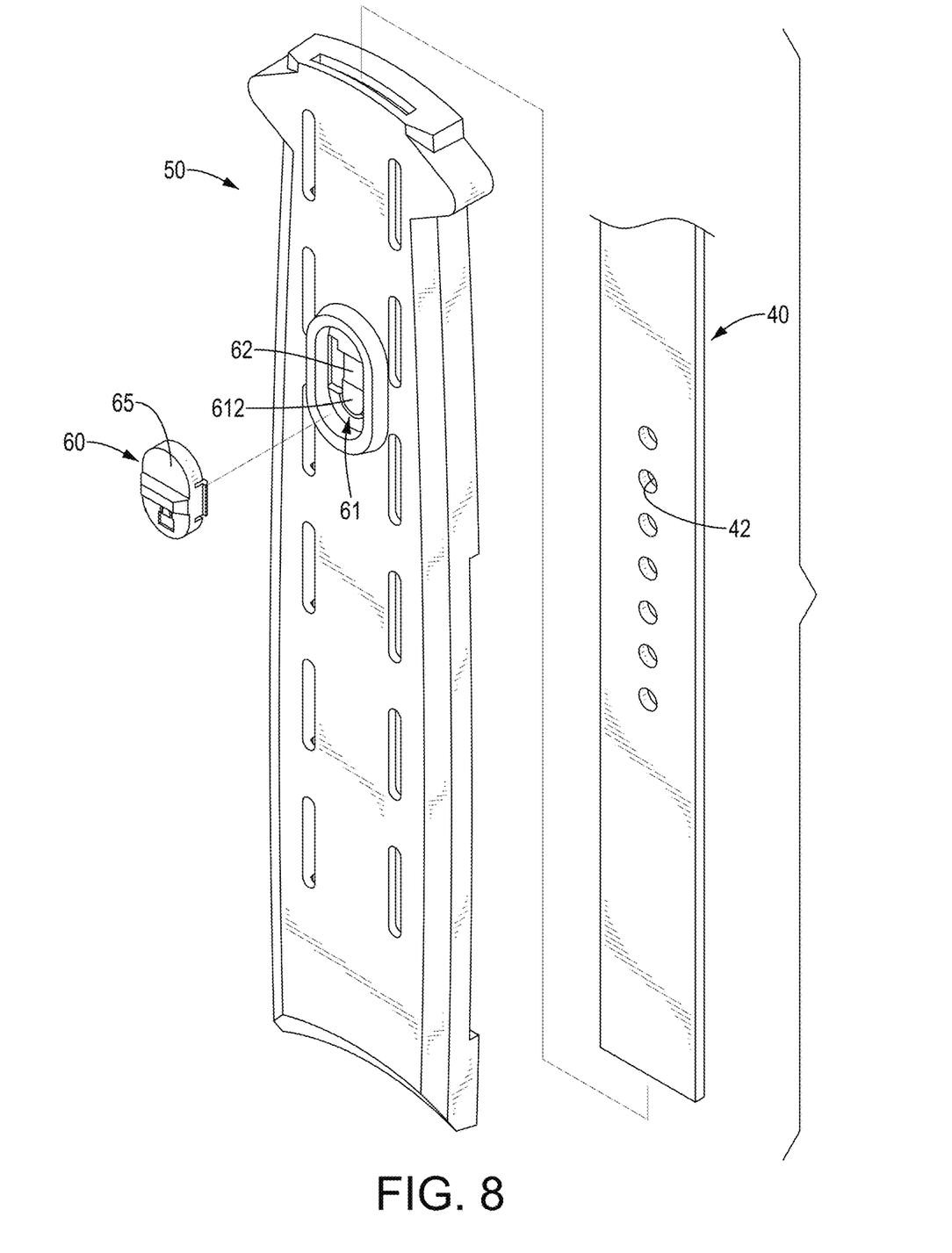
FIG. 8 is an enlarged exploded perspective view of the lumbar support belt in FIG. 7.
Figure 9:
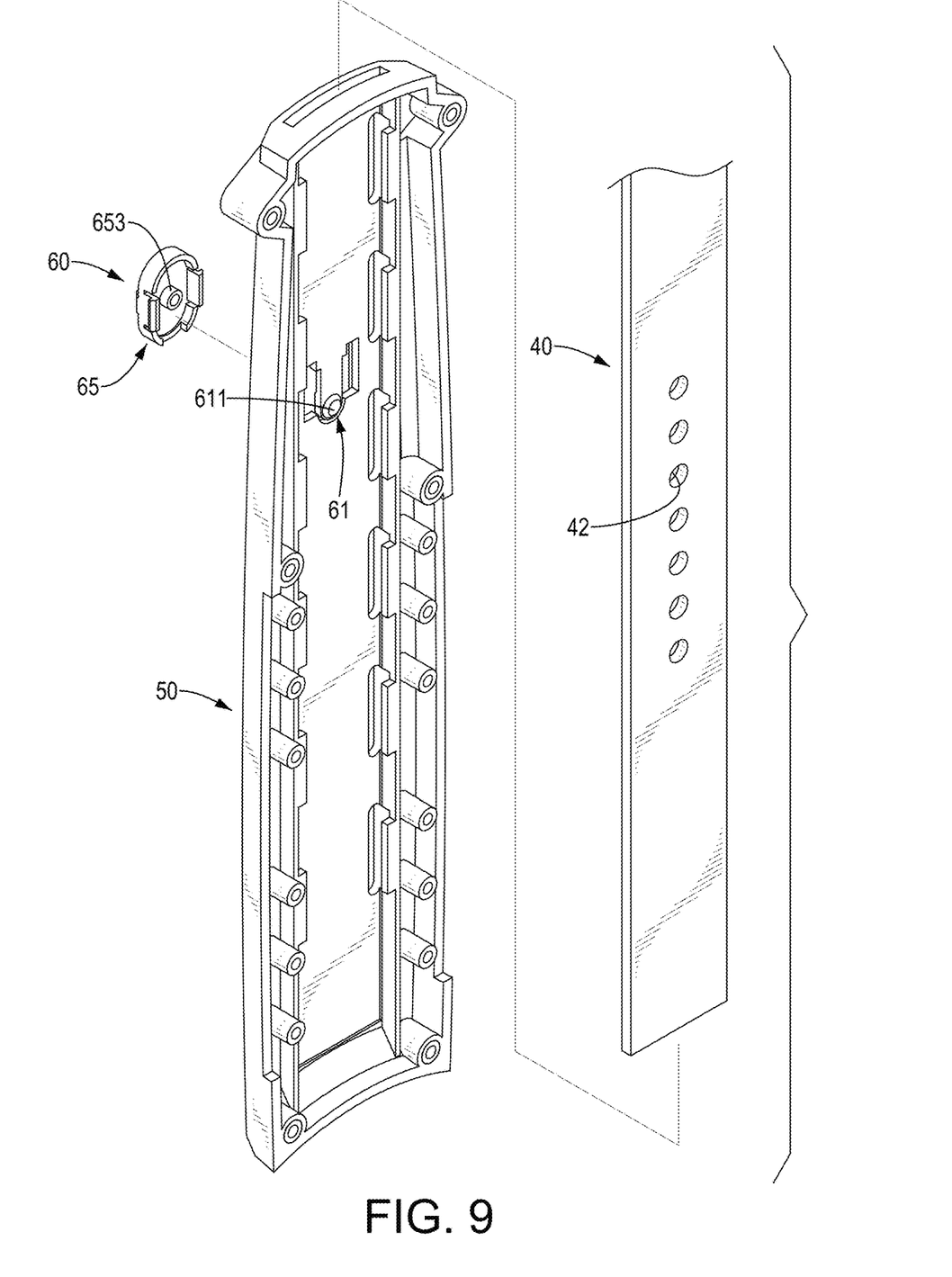
FIG. 9 is another enlarged exploded perspective view of the lumbar support belt in FIG. 7.

The tightening part 30 wraps around the routing portions 23 of the two belt bodies 20 to connect the two belt bodies 20 and has two pulling segments 32 respectively extending toward the two belt bodies 20. With reference to FIG. 6, the two belt bodies 20 are driven to move toward each other by pulling the two pulling segments 32 of the tightening part 30 to move away from the backing plate 10. During the movements of the two belt bodies 20, the sliding wheels 25 of each one of the two belt bodies 20 slide along the sliding channels 12L/12R of the backing plate 10 toward the other one of the two belt bodies 20, thereby limiting moving paths of the two belt bodies 20, avoiding misalignment of the two belt bodies 20, and reducing resistance during the movement of the two belt bodies 20 sliding relative to the backing plate 10. Accordingly, tightness adjustment of the lumbar support belt is easy, smooth, and effortless.

With reference to FIGS. 1 to 5, each belt body 20 includes a tab 21 and a band 22. The tab 21 may be made of a plastic material. The multiple routing portions 23 and the at least one sliding wheel 25 are disposed at the tab 21. The multiple routing portions 23 may be formed at the tab 21 as an integrated piece. The tab 21 may include at least one rod 24 inserted into and extending out of the at least one sliding wheel 25. An engaging lug 241 is formed at an end of each of the at least one rod 24 extending out of the at least one sliding wheel 25 for limiting a position of the sliding wheel 25. Each rod 24 may include a slit 242 for increasing flexibility of the rod 24, so the sliding wheel 25 is easily moved through the engaging lug 241 to be sleeved on the rod 24. The band 22 may be made of a flexible fabric, connected to the tab 21, and extending away from the backing plate 10. The bands 22 of the two belt bodies 20 may have touch fastening surfaces adhered to and attached to each other for ease of wearing.

Figure 1:
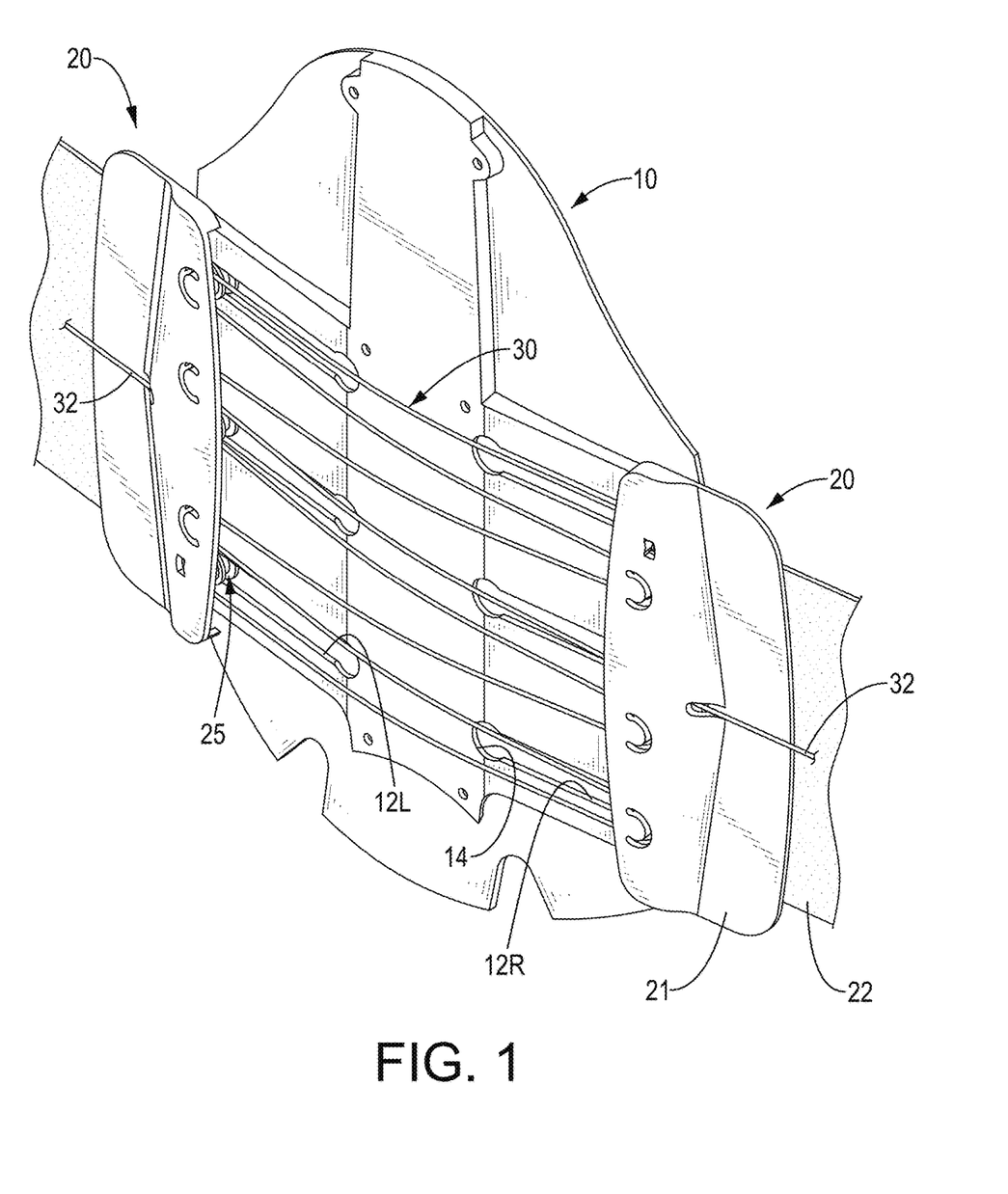
FIG. 1 is an enlarged perspective view of a first embodiment of a lumbar support belt in accordance with the present invention.
Figure 2:
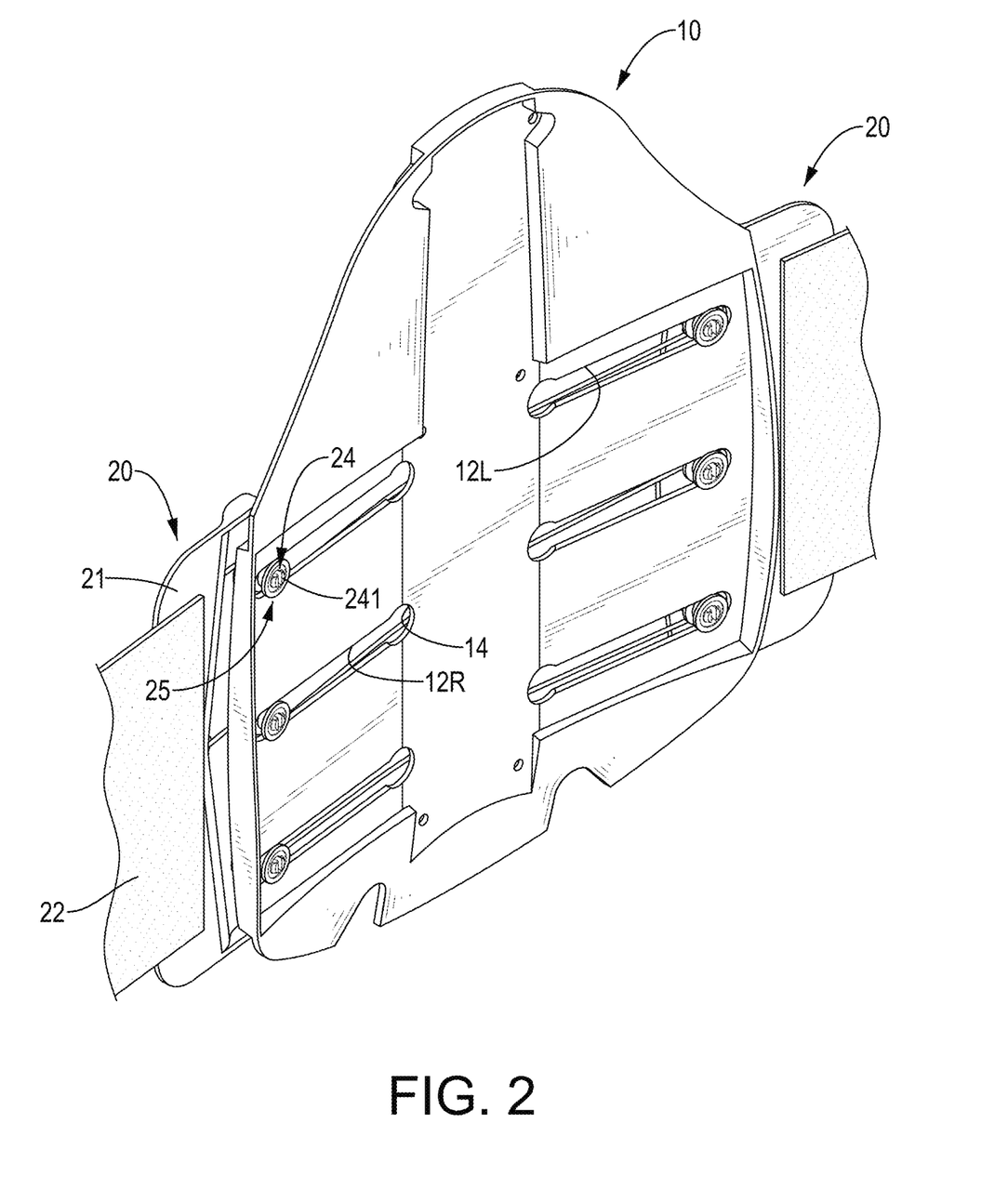
FIG. 2 is another enlarged perspective view of the lumbar support belt in FIG. 1.
Figure 3:
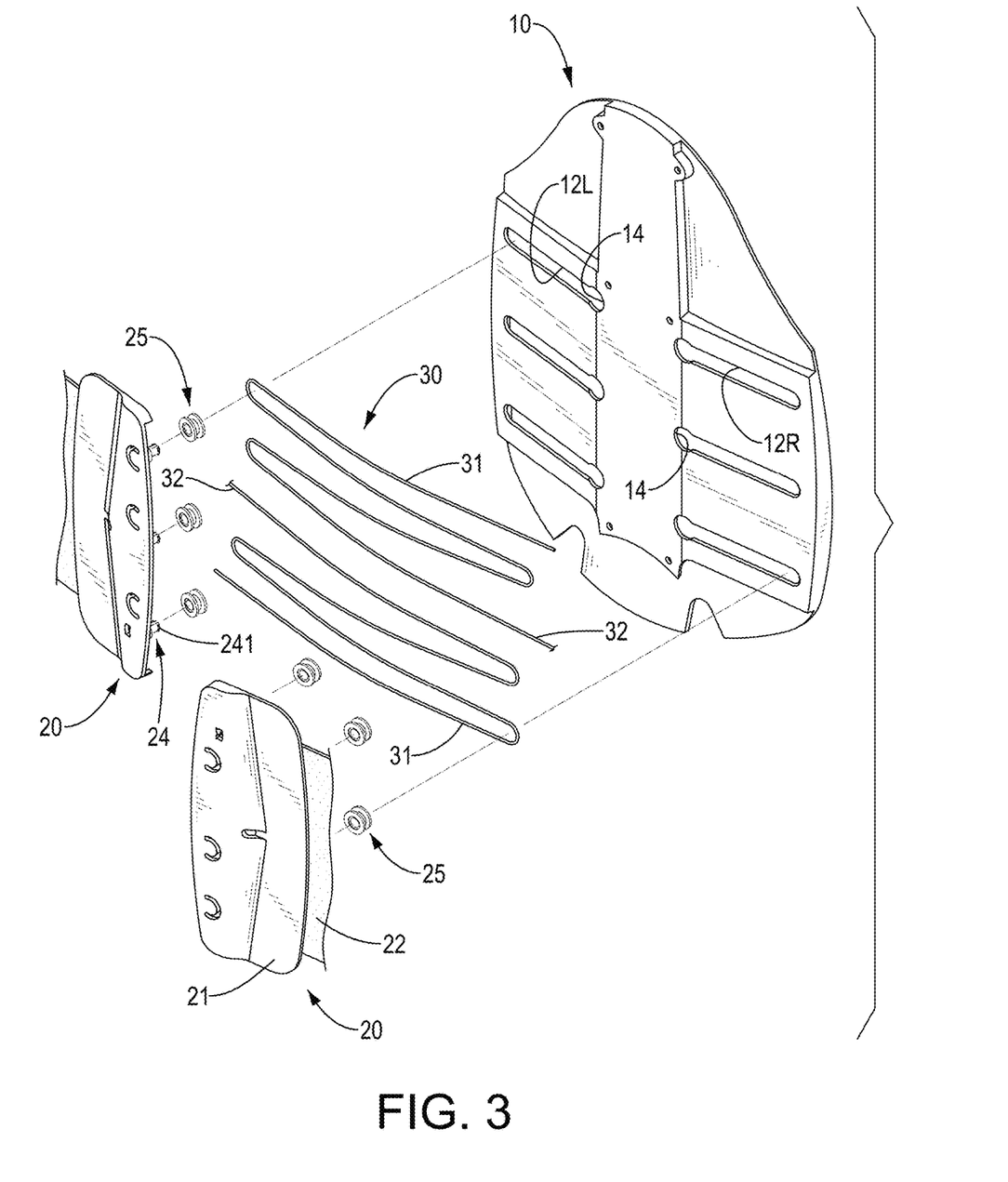
FIG. 3 is an enlarged exploded perspective view of the lumbar support belt in FIG. 1.
Figure 4:
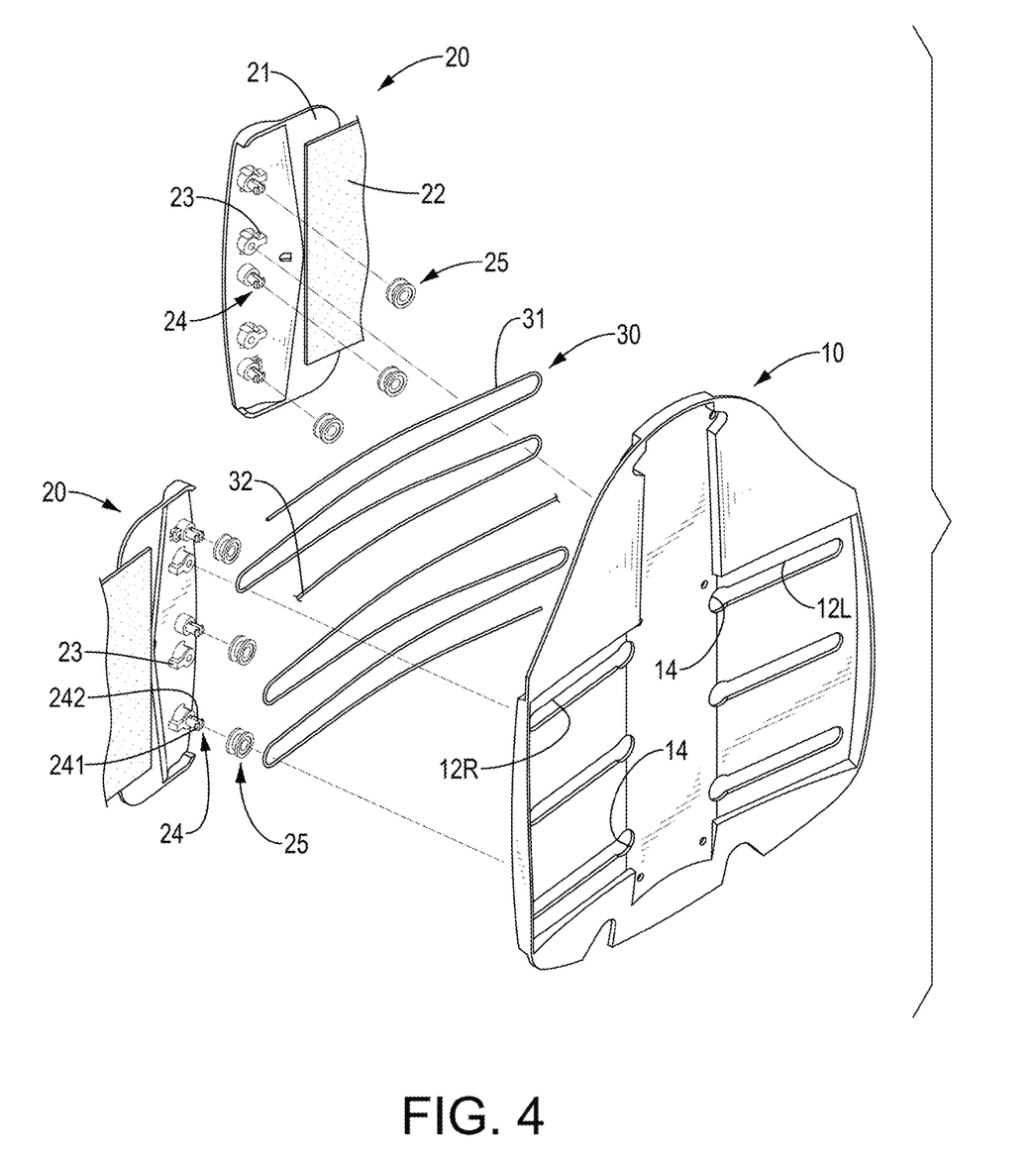
FIG. 4 is another enlarged exploded perspective view of the lumbar support belt in FIG. 1.
Figure 5:
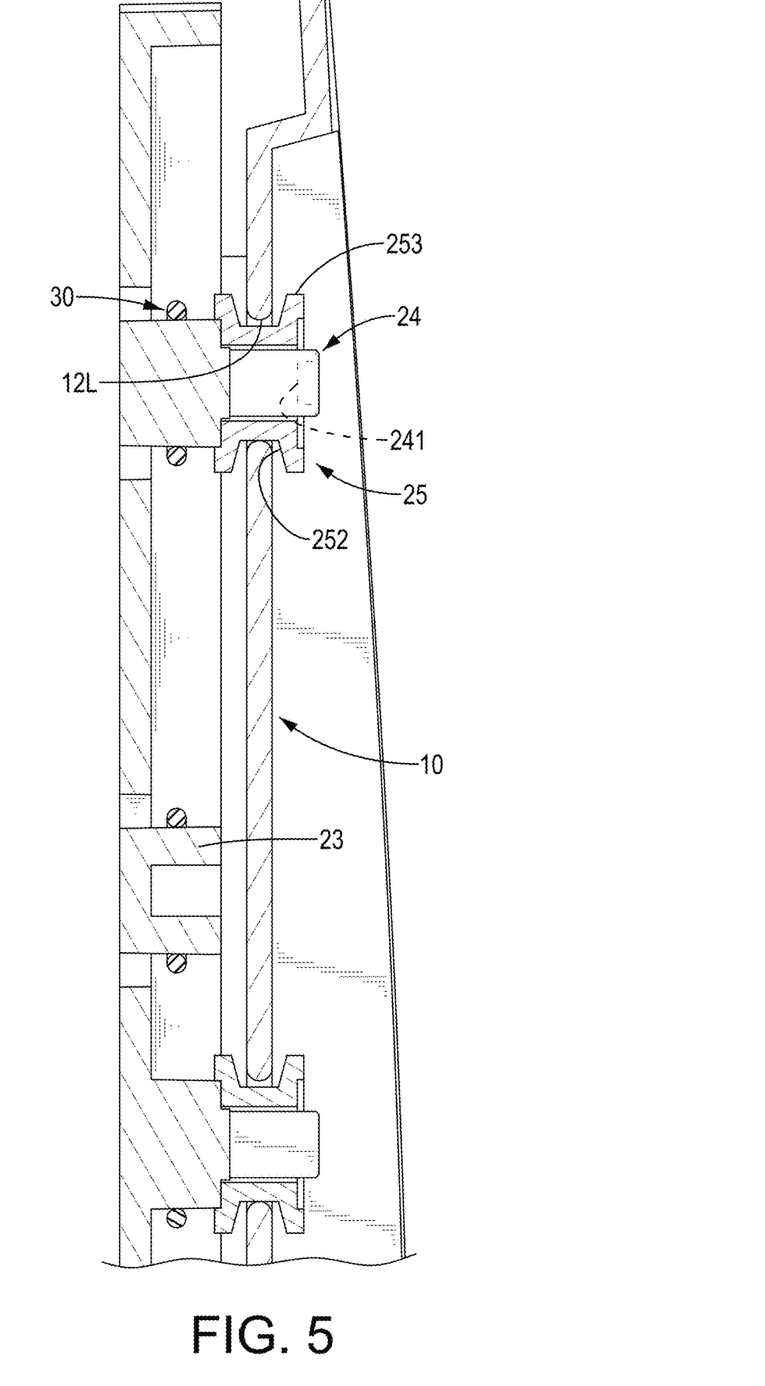
FIG. 5 is an enlarged side view in partial section of the lumbar support belt in FIG. 1.

With reference to FIGS. 5 and 6, each sliding wheel 25 has two flanges 253 respectively located at two opposite ends thereof and a guiding groove 252 formed between the two flanges 253. The two flanges 253 of each sliding wheel 25 extend out of a corresponding sliding channel 12L/12R. Each flange 253 of each sliding wheel 25 has a diameter being larger than a width of the corresponding sliding channel 12L/12R. The backing plate 10 includes multiple inserting openings 14 respectively communicating with the multiple sliding channels 12R/12L. Each inserting opening 14 has a width being larger than the width of each sliding channel 12R/12L and being larger than the diameter of each flange 253 of each sliding wheel 25. Therefore, each sliding wheel 25 can be inserted into a corresponding inserting opening 14 to be moved to the corresponding sliding channel 12L/12R for ease of assembly.

With reference to FIGS. 3 to 6, wrapping style for the tightening part 30 can be varied according to user's need. In the first embodiment, the tightening part 30 includes two string bodies 31. Each string body 31 has an end fixed to one of the two belt bodies 20 and is wrapped around the routing portions 23 of the two belt bodies 20. One of the two string bodies 31 is wrapped downwardly and extends out of one of the two belt bodies 20 to form a pulling segment 32. The other one of the two string bodies 31 is wrapped upwardly and extends out of the other one of the two belt bodies 20 to form another pulling segment 32. The tightening part 30 may be wrapped in other ways for driving the two belt bodies 20 to move toward or away from each other.

With reference to FIGS. 7 to 11, the lumbar support belt further comprises a back brace 40. The back brace 40 is connected to the backing plate 10 and is able to move up and down relative to the backing plate 10. The back brace 40 extends upwardly from the backing plate 10 for supporting a back of the user during wearing the lumbar support belt of the present invention. A length of the back brace 40 extending out of the backing plate 10 can be adjusted according to a height of the user.

A brace holder 50 is connected to the backing plate 10 and partially covers the tightening part 30. The back brace 40 is disposed between the brace holder 50 and the backing plate 10 and has multiple engaging holes 42 arranged top-down at spaced intervals. A lock device 60 is disposed to the brace holder 50 and is selectively engaged with one of the multiple engaging holes 42 of the back brace 40 to keep the back brace 40 in position. Therefore, a position of the back brace 40 relative to the brace holder 50 can be locked and adjusted via the lock device 60 to secure and adjust the length of the back brace 40 extending out of the backing plate 10.

Figure 10:
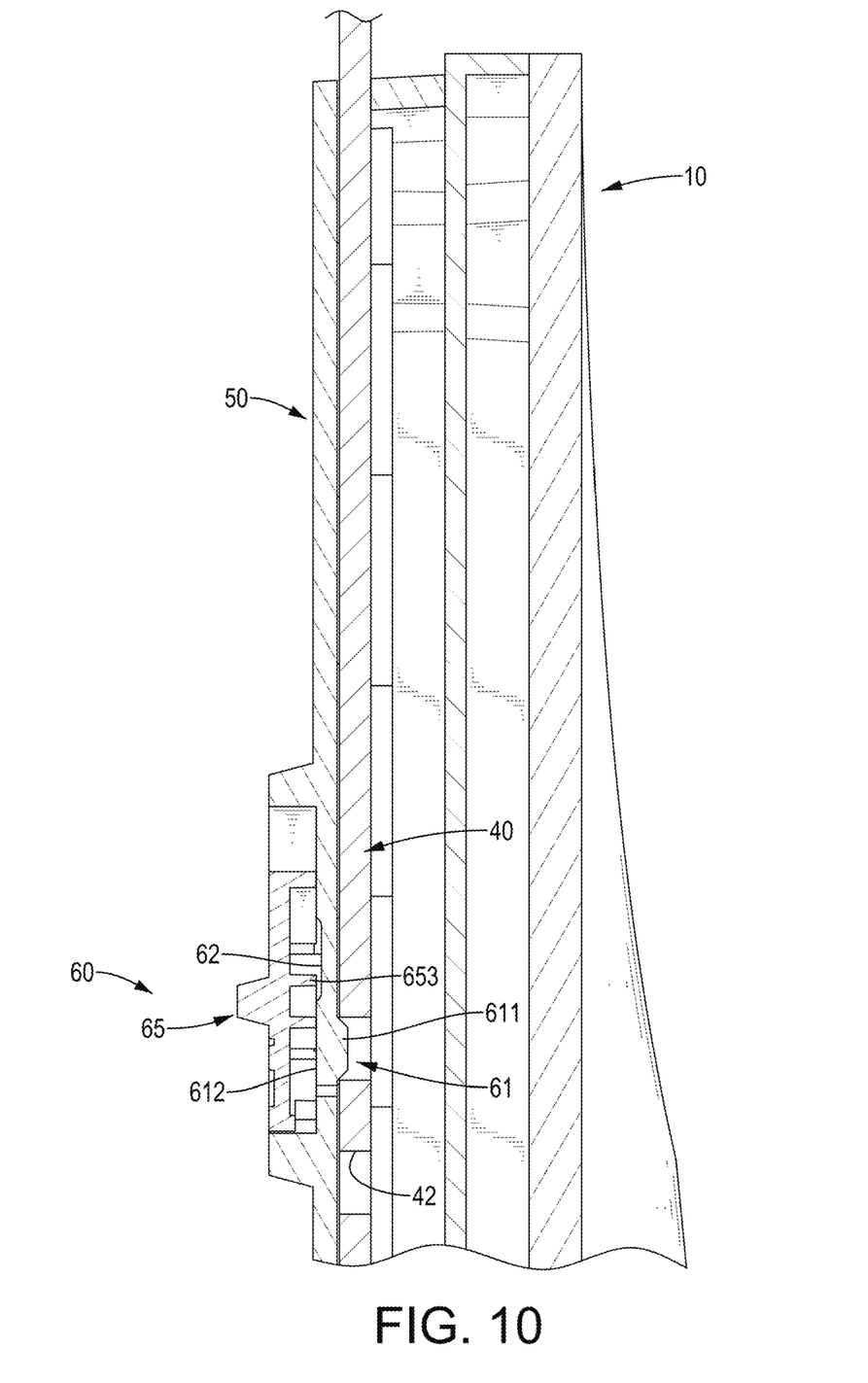
FIG. 10 is an enlarged side view in partial section of the lumbar support belt in FIG. 7.
Figure 11:
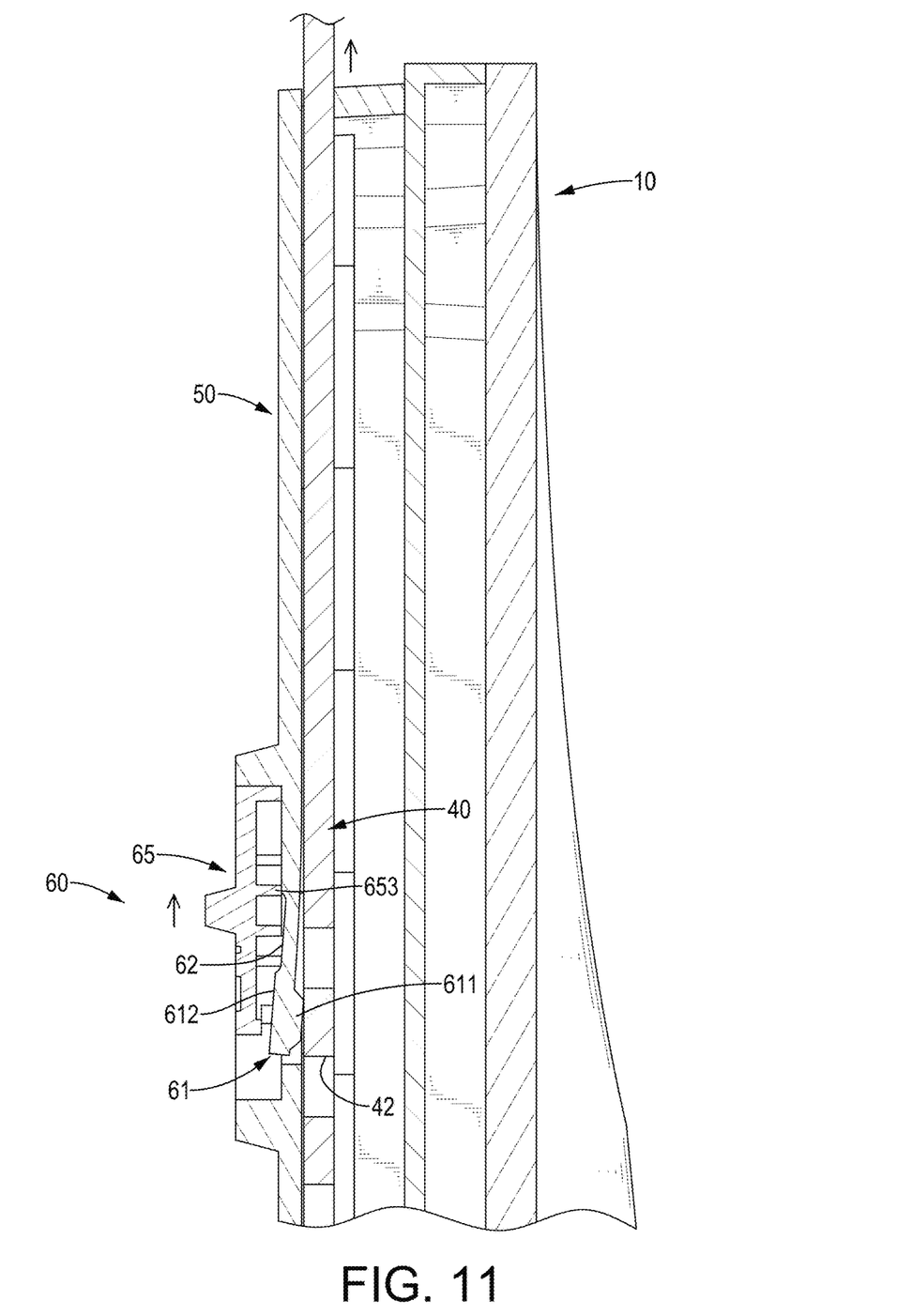
FIG. 11 is an operational enlarged side view in partial section of the lumbar support belt in FIG. 7.

The lock device 60 includes a snap part 61 and a positioning button 65. The snap part 61 is disposed at the brace holder 50 and has a protrusion 611 and an unlock recess 62. The protrusion 611 extends toward the back brace 40 and selectively extends into one of the multiple engaging holes 42 of the back brace 40. An abutting face 612 is formed at a side of the protrusion 611 facing away from the back brace 40. The unlock recess 62 is recessed in a side of the snap part 61 facing away from the back brace 40 and is adjacent to the abutting face 612. The positioning button 65 is slidably connected to the brace holder 50 and has an abutting block 653. With reference to FIG. 10, when the abutting block 653 is moved with the positioning button 65 to face the abutting face 612 of the snap part 61, the protrusion 611 extending into one of the engaging holes 42 of the back brace 40 is blocked by the abutting block 653 and cannot move away from the back brace 40, whereby the snap part 61 is locked by the positioning button 65. With reference to FIG. 11, when the abutting block 653 is moved with the positioning button 65 to face the unlock recess 62 of the snap part 61, the protrusion 611 of the snap part 61 is flexible and movable and is able to separate from the engaging hole 42 of the back brace 40, whereby the snap part 61 is unlocked and the back brace 40 is adjustable.

Since the two belt bodies 20 are moved relative to the backing plate 10 via the sliding wheels 25 moving along the sliding channels 12L/12R of the backing plate 10, resistances during sliding movement between the two belt bodies 20 and the backing plate 10 are reduced. The tightening part 30 only needs to be slightly pulled to drive the two belt bodies 20 to slide relative to the backing plate 10. Accordingly, tightness adjustment of the lumbar support belt in accordance with the present invention is easy, smooth, and effortless. Since the two belt bodies 20 are moved relative to the backing plate 10 via the sliding wheels 25 moving along the sliding channels 12L/12R of the backing plate 10, misalignment of the two belt bodies 20 while pulling the tightening part 30 to move the two belt bodies 20 is reduced.

What is claimed is:

1. A lumbar support belt comprising:
   a backing plate including
      at least one sliding channel extending horizontally;

two belt bodies respectively connected to a left side and a right side of the backing plate, each of the two belt bodies including
- multiple routing portions arranged top-down at spaced intervals; and
- at least one sliding wheel disposed in the at least one sliding channel;

a tightening part wrapped around the routing portions of the two belt bodies to connect the two belt bodies and having
- two pulling segments respectively extending toward the two belt bodies; wherein the at least one sliding wheel of one of the belt bodies slides along the at least one sliding channel of the backing plate toward the other one of the two belt bodies while pulling the two pulling segments of the tightening part away from the backing plate; the lumbar support belt comprises a back brace connected to the backing plate and is able to move up and down relative to the backing plate; a brace holder is fixed to the backing plate; the back brace is disposed between the brace holder and the backing plate and has multiple engaging holes arranged top-down at spaced intervals; a lock device is disposed to the brace holder and is selectively engaged with one of the multiple engaging holes of the back brace to keep the back brace in position; the lock device includes a snap part and a positioning button; the snap part is disposed at the brace holder and has a protrusion and an unlock recess; the protrusion extends toward the back brace and selectively extends into one of the multiple engaging holes of the back brace; an abutting face is formed at a side of the protrusion facing away from the back brace; the unlock recess is recessed in a side of the snap part facing away from the back brace and is adjacent to the abutting face; and the positioning button is slidably connected to the brace holder and has an abutting block selectively blocking the protrusion.

2. The lumbar support belt as claimed in claim 1, wherein each of the two belt bodies includes a tab and a band; and
the multiple routing portions and the at least one sliding wheel of each of the two belt bodies are disposed at the tab of the belt body;
the band of each of the two belt bodies is connected to the tab of the belt body and extends away from the backing plate.

3. The lumbar support belt as claimed in claim 2, wherein the tab of each of the two belt bodies includes at least one rod respectively extending into and extending out of the at least one sliding wheel of the belt body; and
an engaging lug is formed at an end of the at least one rod of the tab of each of the two belt bodies extending out of a corresponding one of the at least one sliding wheel.

4. The lumbar support belt as claimed in claim 3, wherein the at least one sliding channel of the backing plate includes multiple sliding channels spaced apart from one another.

5. The lumbar support belt as claimed in claim 3, wherein
the at least one sliding channel of the backing plate includes multiple sliding channels adjacent to the left side of the backing plate and arranged top-down at spaced intervals and multiple sliding channels adjacent to the right side of the backing plate and arranged top-down at spaced intervals;
the at least one sliding wheel of each of the two belt bodies includes multiple sliding wheels;
the multiple sliding wheels of one of the two belt bodies are respectively disposed in the multiple sliding channels adjacent to the left side of the backing plate; and
the multiple sliding wheels of the other one of the two belt bodies are respectively disposed in the multiple sliding channels adjacent to the right side of the backing plate.

6. The lumbar support belt as claimed in claim 5, wherein
each sliding wheel has two flanges and a guiding groove formed between the two flanges;
the two flanges of each sliding wheel extend out of a corresponding sliding channel;
each flange of each sliding wheel has a diameter being larger than a width of the corresponding sliding channel;
the backing plate includes multiple inserting openings respectively communicating with the multiple sliding channels; and
each inserting opening has a width being larger than the width of each sliding channel and being larger than the diameter of each of the two flanges of each sliding wheel.

7. The lumbar support belt as claimed in claim 2, wherein the at least one sliding channel of the backing plate includes multiple sliding channels spaced apart from one another.

8. The lumbar support belt as claimed in claim 2, wherein
the at least one sliding channel of the backing plate includes multiple sliding channels adjacent to the left side of the backing plate and arranged top-down at spaced intervals and multiple sliding channels adjacent to the right side of the backing plate and arranged top-down at spaced intervals;
the at least one sliding wheel of each of the two belt bodies includes multiple sliding wheels;
the multiple sliding wheels of one of the two belt bodies are respectively disposed in the multiple sliding channels adjacent to the left side of the backing plate; and
the multiple sliding wheels of the other one of the two belt bodies are respectively disposed in the multiple sliding channels adjacent to the right side of the backing plate.

9. The lumbar support belt as claimed in claim 8, wherein
each sliding wheel has two flanges and a guiding groove formed between the two flanges;
the two flanges of each sliding wheel extend out of a corresponding sliding channel;
each flange of each sliding wheel has a diameter being larger than a width of the corresponding sliding channel;
the backing plate includes multiple inserting openings respectively communicating with the multiple sliding channels; and
each inserting opening has a width being larger than the width of each sliding channel and being larger than the diameter of each of the two flanges of each sliding wheel.

10. The lumbar support belt as claimed in claim 1, wherein the at least one sliding channel of the backing plate includes multiple sliding channels spaced apart from one another.

11. The lumbar support belt as claimed in claim 1, wherein
the at least one sliding channel of the backing plate includes multiple sliding channels adjacent to the left side of the backing plate and arranged top-down at spaced intervals and multiple sliding channels adjacent to the right side of the backing plate and arranged top-down at spaced intervals;

the at least one sliding wheel of each of the two belt bodies includes multiple sliding wheels;

the multiple sliding wheels of one of the two belt bodies are respectively disposed in the multiple sliding channels adjacent to the left side of the backing plate; and the multiple sliding wheels of the other one of the two belt bodies are respectively disposed in the multiple sliding channels adjacent to the right side of the backing plate.

12. The lumbar support belt as claimed in claim 11, wherein each sliding wheel has two flanges and a guiding groove formed between the two flanges;

the two flanges of each sliding wheel extend out of a corresponding sliding channel;

each flange of each sliding wheel has a diameter being larger than a width of the corresponding sliding channel;

the backing plate includes multiple inserting openings respectively communicating with the multiple sliding channels; and each inserting opening has a width being larger than the width of each sliding channel and being larger than the diameter of each of the two flanges of each sliding wheel.

* * * * *